United States Patent
Zur et al.

(10) Patent No.: US 9,579,042 B2
(45) Date of Patent: *Feb. 28, 2017

(54) SYSTEM AND METHOD FOR FOCUSING OF HIGH INTENSITY FOCUSED ULTRASOUND BASED ON MAGNETIC RESONANCE—ACOUSTIC RADIATION FORCE IMAGING FEEDBACK

(71) Applicant: General Electric Company, Schenectady, NY (US)

(72) Inventors: Yuval Zur, Haifa (IL); William Grissom, Nashville, TN (US)

(73) Assignee: GENERAL ELECTRIC COMPANY, Schenectady, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 14/803,370

(22) Filed: Jul. 20, 2015

(65) Prior Publication Data

US 2015/0320335 A1 Nov. 12, 2015

Related U.S. Application Data

(63) Continuation of application No. 13/900,670, filed on May 23, 2013, now Pat. No. 9,119,955.

(51) Int. Cl.
*A61B 5/055* (2006.01)
*G01R 33/561* (2006.01)
(Continued)

(52) U.S. Cl.
CPC ...... *A61B 5/055* (2013.01); *A61B 17/320068* (2013.01); *A61B 90/37* (2016.02);
(Continued)

(58) Field of Classification Search
CPC ...... A61B 17/320068; A61B 2090/374; A61B 2090/378; A61B 5/055; A61B 90/37;
(Continued)

(56) References Cited

U.S. PATENT DOCUMENTS 9,119,955 B2 * 9/2015 Zur ..................... A61N 7/02
2011/0270136 A1 11/2011 Vitek et al.

OTHER PUBLICATIONS

Vogel et al., "Use of Fast Spin Echo for Phase Shift Magnetic Resonance Thermometry," Journal of Magnetic Resonance Imaging, vol. 18, 2003, pp. 507-512.
(Continued)

*Primary Examiner* — Michael Rozanski

(57) ABSTRACT

A system and method for MR imaging is disclosed. The method causes an RF coil assembly and plurality of gradient coils to apply a fast spin echo (FSE) pulse sequence comprising a preparation segment and a plurality of refocusing segments. The FSE pulse sequence generates a pair of echoes is generated in each of the plurality of refocusing segments that comprises a first echo generated by magnetization pathways having an even number of phase inversions and a second echo generated by magnetization pathways having an even number of phase inversions. MR signals are acquired from the first echo and the second echo and an image of at least a portion of a subject of interest is reconstructed from the acquired MR signals.

20 Claims, 12 Drawing Sheets

(51) Int. Cl.
  G01R 33/48    (2006.01)
  G01R 33/385   (2006.01)
  A61B 17/32    (2006.01)
  A61B 19/00    (2006.01)
  A61N 7/02     (2006.01)
  A61N 7/00     (2006.01)

(52) U.S. Cl.
  CPC .............. *A61N 7/02* (2013.01); *G01R 33/385* (2013.01); *G01R 33/4814* (2013.01); *G01R 33/5617* (2013.01); *A61B 2090/374* (2016.02); *A61B 2090/378* (2016.02); *A61N 2007/0086* (2013.01)

(58) Field of Classification Search
  CPC .............. A61N 2007/0086; A61N 7/02; G01R 33/385; G01R 33/4814; G01R 33/5617
  See application file for complete search history.

(56) References Cited

OTHER PUBLICATIONS

Williams et al., "A Novel Fast Split-Echo Multi-Shot Diffusion-Weighted MRI Method Using Navigator Echoes," Magnetic Resonance in Medicine, vol. 41, 1999, pp. 734-742.

Schick, "Splice: Sub-Second Diffusion-Sensitive MR Imaging Using a Modified Fast Spin-Echo Acquisition Mode," MRM, vol. 38, 1997, pp. 638-644.

Norris et al., "On the Application of Ultra-fast Rare Experiments," Magnetic Resonance in Medicine, vol. 27, 1992, pp. 142-164.

Zur et al., "A Phase-Cycling Technique for Canceling Spurious Echoes in NMR Imaging," Journal of Magnetic Resonance, vol. 71, 1987, pp. 212-228.

Marsac et al., "MR-guided adaptive focusing of therapeutic ultrasound beams in the human head," Medical Physics, vol. 39, No. 2, Feb. 2012, pp. 1141-1149.

Grissom et al., "Rapid HIFU autofocusing using the entire MR-ARFI image," AIP Conference Proceedings, 12th International Symposium on Therapeutic Ultrasound, 2012, pp. 162-167.

Hertzberg et al., "Ultrasound focusing using magnetic resonance acoustic radiation force imaging: Application to ultrasound transcranial therapy," Medical Physics, vol. 37, No. 6, Jun. 2010, pp. 2934-2942.

Larrat et al., "MR-Guided Adaptive Focusing of Ultrasound," IEEE Transactions on Ultrasonics, Ferroelectrics, and Frequency Control, vol. 57, No. 8, Aug. 2010, pp. 1734-1747.

Paxman et al., "Joint estimation of object and aberrations by using phase diversity," J. Opt. Soc. Am. A, vol. 9, No. 7, Jul. 1992, pp. 1072-1085.

Aarnio et al., "A New Ultrasound Method for Determining the Acoustic Phase Shifts Caused by the Skull Bone," Ultrasound in Medicine and Biology, vol. 31, No. 6, 2005, pp. 771-780.

* cited by examiner

SYSTEM AND METHOD FOR FOCUSING OF HIGH INTENSITY FOCUSED ULTRASOUND BASED ON MAGNETIC RESONANCE—ACOUSTIC RADIATION FORCE IMAGING FEEDBACK

CROSS-REFERENCE TO RELATED APPLICATION

The present application is a continuation of and claims priority to U.S. Pat. No. 9,119,955 issued on Sep. 1, 2015, the disclosure of which is incorporated herein by reference in its entirety.

BACKGROUND OF THE INVENTION

Embodiments of the invention relate generally to high intensity focused ultrasound (HIFU), and more specifically, to a system and method of employing magnetic resonance—acoustic radiation force impulse (MR-ARFI) imaging feedback for fast and robust focusing of the HIFU.

Focused ultrasound therapy involves delivering ultrasound energy to localized regions of tissue from externally (non-invasive) or internally (minimally-invasive) located transducers. The amount of ultrasound energy delivered to tissue dictates the nature of the biologic effect produced at that location. At high intensities with continuous exposure, ultrasound energy can generate enough heat to cause irreversible thermal damage through coagulation. As the exposure is reduced in duty cycle to short pulses, the mechanical energy associated with ultrasound dominates and can be used to generate a range of bio-effects, including: vascular occlusion or hemorrhage, permeation of cells, and tissue-homogenization.

For this purpose, a piezo-ceramic transducer is placed externally to the patient, but in close proximity to the tissue to be ablated (the "target"). The transducer converts an electronic drive signal into mechanical vibrations, resulting in the emission of acoustic waves (a process hereinafter referred to as "sonication"). The transducer may be shaped so that the waves converge in a focal zone. Alternatively or additionally, the transducer may be formed of a plurality of individually driven transducer elements whose phases (and, optionally, amplitudes) can each be controlled independently from one another and, thus, can be set so as to result in constructive interference of the individual acoustic waves in the focal zone. Such a "phased-array" transducer facilitates steering the focal zone to different locations by adjusting the relative phases between the transducers, and generally provides the higher a focus quality and resolution, the greater the number of transducer elements. Magnetic resonance imaging (MRI) may be utilized to visualize the focus and target in order to guide the ultrasound beam.

The relative phases at which the transducer elements need to be driven to result in a focus at the target location depend on the relative location and orientation of the transducer surface and the target, as well as on the dimensions and acoustic material properties (e.g., sound velocities) of the tissue or tissues between them (i.e., the "target tissue"). Thus, to the extent the geometry and acoustic material properties are known, the relative phases (and, optionally, amplitudes) can be calculated. In practice, however, knowledge of these parameters is often too incomplete or imprecise to enable high-quality focusing based on computations of the relative phases alone. For example, when ultrasound is focused into the brain to treat a tumor, the skull in the acoustic path may cause aberrations that are not readily ascertainable. In such situations, treatment is typically preceded by an auto-focusing procedure in which, iteratively, an ultrasound focus is generated at or near the target, the quality of the focus is measured (using, e.g., thermal imaging or acoustic radiation force impulse (ARFI) imaging), and experimental feedback is used to adjust the phases of the transducer elements to achieve sufficient focus quality.

The number of sonications in such an auto-focusing procedure is typically at least three times the number of individually controlled transducer elements, and even more sonications may be needed to overcome measurement noise. For example, for a transducer array with 1,000 elements, auto-focusing typically involves a systematic series of 3,000 or more sonications to optimize the focus thereof. The auto-focusing procedure may thus take a substantial amount of time, which may render it impracticable or, at the least, inconvenient for a patient. Further, during the auto-focusing sonications, ultrasound energy is inevitably deposited into the tissue at and surrounding the target, potentially damaging healthy tissue.

Attempts have previously been made to improve the auto-focusing procedure using MR-ARFI to measure the quality of the focus, with such MR-ARFI techniques being employed both to reduce the time required for performing the procedure and to minimize the effect of pre-therapeutic sonications. For example, a previous attempt for autofocusing using MR-ARFI is described in "Ultrasound focusing using magnetic resonance acoustic radiation force imaging: Application to ultrasound transcranial therapy" to Y. Hertzberg et al., Med Phys, Vol. 37, No. 6, 2010, in which the array of ultrasound transducers was divided into n groups (i.e., sub-arrays)—with it being assumed that all transducers in each group are approximately the same. The phase/amplitude of each group of transducers was then randomly changed until a reasonable focus was achieved. The method described by Hertzberg et al., however, is still time consuming and is less systematic than is desired. That is, the method described in Hertzberg et al. disregards MR-ARFI measurements at all voxels other than the center of the focus, such that a large number of image acquisitions are still required.

It would therefore be desirable to provide a system and method for MR-ARFI-based autofocusing of a phased array of transducer element to create a high-quality ultrasound focus. It would also be desirable for such a system and method to reduce the number of image acquisitions required to perform the autofocusing so as to reduce the time required for performing the autofocusing procedure and to minimize the effect of pre-therapeutic sonications, thereby making the MR-ARFI-based autofocusing clinically-feasible, and possible in near-real time.

BRIEF DESCRIPTION OF THE INVENTION

In accordance with one aspect of the invention, a magnetic resonance (MR) imaging system includes a plurality of gradient coils positioned about a bore of a magnet, an RF coil assembly configured to emit RF pulse sequences and arranged to receive resulting MR signals from a subject of interest, and a system control coupled to the plurality of gradient coils and the RF coil assembly, the system control programmed to control the RF coil assembly and the plurality of gradient coils to apply a fast spin echo (FSE) pulse sequence comprising a preparation segment and a plurality of refocusing segments, wherein a pair of echoes is generated in each of the plurality of refocusing segments that comprises a first echo generated by magnetization pathways having an even number of phase inversions and a second echo generated by magnetization pathways having an even number of phase inversions. The MR imaging system also includes a computer programmed to acquire the MR signals from the first echo and the second echo and reconstruct an image of at least a portion of the subject of interest from the acquired MR signals.

In accordance with another aspect of the invention, a method for magnetic resonance (MR) imaging includes causing an MR imaging system to apply a fast spin echo (FSE) pulse sequence comprising a preparation segment and a plurality of refocusing segments, wherein applying the FSE pulse sequence further includes applying a 90° RF pulse in the preparation segment and applying a 180° RF pulse in each of the plurality of refocusing segments. The method also includes causing the MR imaging system to acquire MR image data from a pair of echoes in each of the plurality of refocusing segments, the pair of echoes comprising a first echo generated by magnetization pathways having an even number of phase inversions and a second echo generated by magnetization pathways having an even number of phase inversions, and causing a processor in the MR imaging system to generate an image from the acquired MR image data.

In accordance with yet another aspect of the invention, a non-transitory computer readable storage medium is provided having stored thereon a computer program comprising instructions that, when executed by a computer, cause the computer to request transmission of a 90° RF pulse during a preparation segment of a fast spin echo (FSE) pulse sequence and request transmission of a 180° RF pulse during each of a plurality of refocusing segments of the FSE pulse sequence, with each 180° RF pulse generating a first echo and a second echo in its respective refocusing segment. The instructions further cause the computer to separate the first echo from the second echo, acquire magnetic resonance (MR) signals from the first and second echoes, calculate a phase difference between the MR signals from the separated first and second echoes, combine the MR signals from the separated first and second echoes based on the phase difference there between in order to reduce a signal-to-noise ratio (SNR) of the MR signals, and generate an MR image based on the MR signals.

Various other features and advantages will be made apparent from the following detailed description and the drawings.

BRIEF DESCRIPTION OF THE DRAWINGS

The drawings illustrate embodiments presently contemplated for carrying out the invention.

In the drawings.

DETAILED DESCRIPTION

Embodiments of the invention are directed to a high intensity focused ultrasound (HIFU) system and associated magnetic resonance (MR) imaging system and that employs magnetic resonance—acoustic radiation force impulse (MR-ARFI) imaging feedback for fast and robust focusing of the HIFU.

Figure 1:
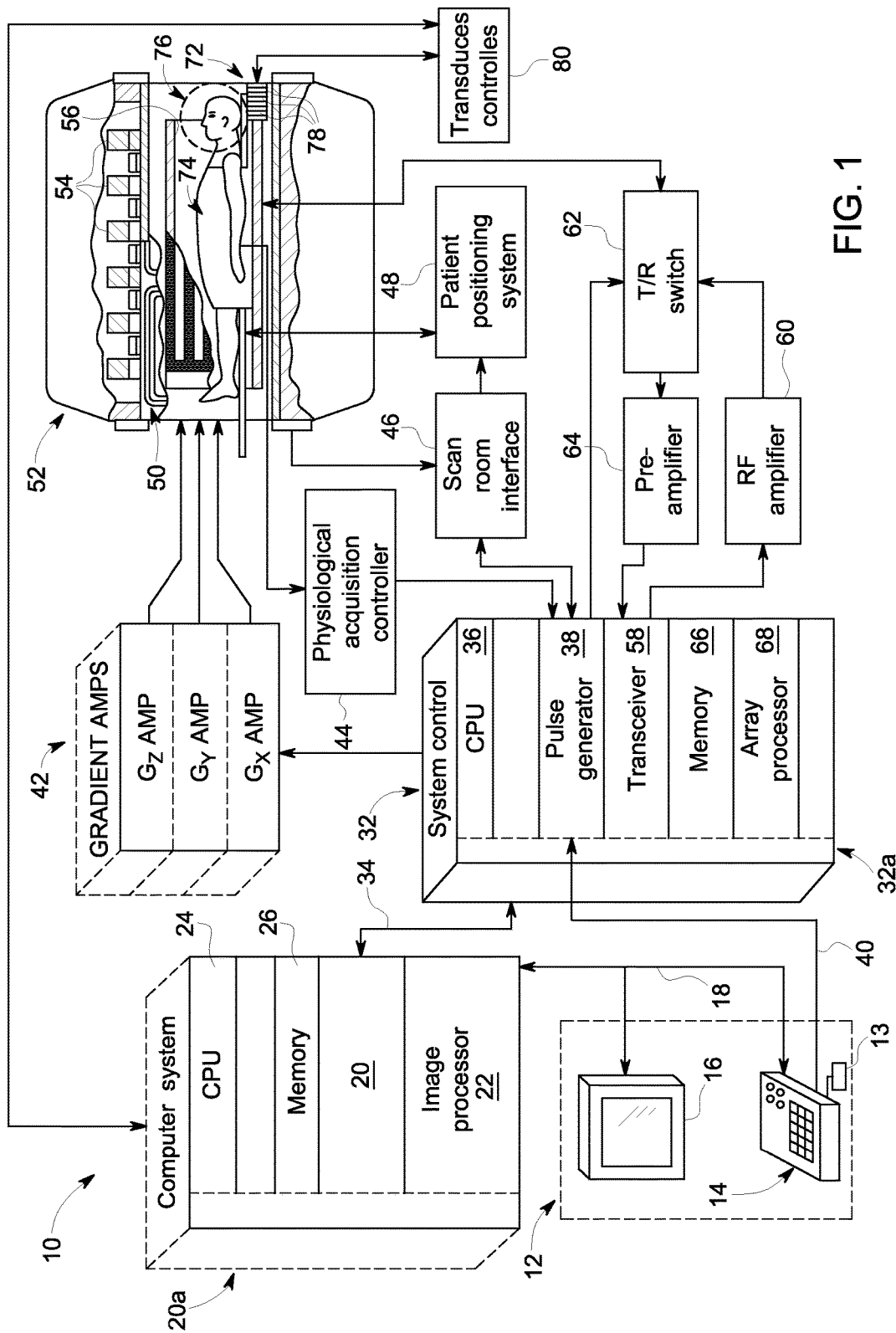
FIG. 1 is a schematic block diagram of an exemplary MR imaging system and focused ultrasound system for use with an embodiment of the invention.

Referring to FIG. 1, the major components of an MR imaging system 10 and a focused ultrasound system 70 (i.e., HIFU system) are shown incorporating an embodiment of the invention. With regard first to the MR imaging system 10, the operation of the system is controlled for certain functions from an operator console 12 which in this example includes a keyboard or other input device 13, a control panel 14, and a display screen 16. The console 12 communicates through a link 18 with a separate computer system 20 that enables an operator to control the production and display of images on the display screen 16. The computer system 20 includes a number of modules which communicate with each other through a backplane 20a. These modules include an image processor module 22, a CPU module 24 and a memory module 26, known in the art as a frame buffer for storing image data arrays. The computer system 20 communicates with a separate system control 32 through a high speed serial link 34. The input device 13 can include a mouse, joystick, keyboard, track ball, touch activated screen, light wand, voice control, card reader, push-button, or any similar or equivalent input device, and may be used for interactive geometry prescription.

The system control 32 includes a set of modules connected together by a backplane 32a. These include a CPU module 36 and a pulse generator module 38 which connects to the operator console 12 through a serial link 40. It is through link 40 that the system control 32 receives commands from the operator to indicate the scan sequence that is to be performed. The pulse generator module 38 operates the system components to carry out the desired scan sequence and produces data which indicates the timing, strength and shape of the RF pulses produced, and the timing and length of the data acquisition window. The pulse generator module 38 connects to a set of gradient amplifiers 42, to indicate the timing and shape of the gradient pulses that are produced during the scan. The pulse generator module 38 can also receive patient data from a physiological acquisition controller 44 that receives signals from a number of different sensors connected to the patient, such as ECG signals from electrodes attached to the patient. And finally, the pulse generator module 38 connects to a scan room interface circuit 46 which receives signals from various sensors associated with the condition of the patient and the magnet system. It is also through the scan room interface circuit 46 that a patient positioning system 48 receives commands to move the patient to the desired position for the scan.

The gradient waveforms produced by the pulse generator module 38 are applied to the gradient amplifier system 42 having Gx, Gy, and Gz amplifiers. Each gradient amplifier excites a corresponding physical gradient coil in a gradient coil assembly generally designated 50 to produce the magnetic field gradients used for spatially encoding acquired signals. The gradient coil assembly 50 forms part of a resonance assembly 52 which includes a polarizing magnet 54 and a whole-body RF coil 56. A transceiver module 58 in the system control 32 produces pulses which are amplified by an RF amplifier 60 and coupled to the RF coil 56 by a transmit/receive switch 62. The resulting signals emitted by the excited nuclei in the patient may be sensed by the same RF coil 56 and coupled through the transmit/receive switch 62 to a preamplifier 64. The amplified MR signals are demodulated, filtered, and digitized in the receiver section of the transceiver 58. The transmit/receive switch 62 is controlled by a signal from the pulse generator module 38 to electrically connect the RF amplifier 60 to the coil 56 during the transmit mode and to connect the preamplifier 64 to the coil 56 during the receive mode. The transmit/receive switch 62 can also enable a separate RF coil (for example, a surface coil) to be used in either the transmit or receive mode.

The MR signals picked up by the RF coil 56 are digitized by the transceiver module 58 and transferred to a memory module 66 in the system control 32. A scan is complete when an array of raw k-space data has been acquired in the memory module 66. This raw k-space data is rearranged into separate k-space data arrays for each image to be reconstructed, and each of these is input to an array processor 68 which operates to Fourier transform the data into an array of image data. This image data is conveyed through the serial link 34 to the computer system 20 where it is stored in memory. In response to commands received from the operator console 12 or as otherwise directed by the system software, this image data may be archived in long term storage or it may be further processed by the image processor 22 and conveyed to the operator console 12 and presented on the display 16.

With regard to the focused ultrasound system 70, the system is positioned, at least in part, adjacent to (or within the bore of) MRI system 10. The focused ultrasound system includes an ultrasound transducer 72, which is disposed near a subject of interest 74 and directed towards a target 76 in a region of interest ("ROI") inside the patient. The transducer 72 may comprise a one- or two-dimensional array (i.e., a row or a matrix) of individually controllable transducer elements 78. In other embodiments, the transducer elements 78 may be arranged in a non-coordinated fashion, i.e., they need not be spaced regularly or arranged in a regular pattern. The transducer may have a curved (e.g., spherical or parabolic) shape, as illustrated, or may include one or more planar or otherwise shaped sections. Its dimensions may vary, depending on the application, between millimeters and tens of centimeters. The transducer elements 78 may be piezoelectric ceramic elements. Piezo-composite materials, or generally any materials capable of converting electrical energy to acoustic energy, may also be used. To damp the mechanical coupling between the elements 78, they may be mounted on the housing using silicone rubber or any other suitable damping material.

The transducer elements 78 are separately controllable, i.e., they are each capable of emitting ultrasound waves at amplitudes and/or phases that are independent of the amplitudes and/or phases of the other transducers. A transducer controller 80 in communication with the array serves to drive the transducer elements 78. For n transducer elements 78, the controller 80 may contain n control circuits, each comprising an amplifier and a phase delay circuit and driving one of the transducer elements. The controller 80 may split a radio frequency (RF) input signal, typically in the range from 0.1 MHz to 4 MHz, to provide n channels for the n control circuits. The controller may be configured to drive the individual transducer elements 78 at the same frequency, but at different phases and different amplitudes so that they collectively produce a focused ultrasound beam. The controller 80 may also include additional circuitry and switches that allow subsets of the transducer elements to be grouped into sub-arrays, and the elements within one sub-array to be driven at the same amplitude and phase.

The controller 80 desirably provides computational functionality, which may be implemented in software, hardware, firmware, hardwiring, or any combination thereof, to compute the required phases and amplitudes for a desired focus location. For example, the controller 80 may receive data indicative of the desired focus location (i.e., the target) relative to the ultrasound transducer, and account for the respective distances between each transducer element and the target, and the associated travel times of the acoustic waves that originate at the various transducer elements, in computing the phases. If the sum of the transducer element phase and the phase acquired between the transducer element and the target is the same for all elements, the waves from the different transducer elements constructively interfere at the target.

In general, the controller 80 may include several separable apparatus, such as a frequency generator, a beamformer containing the amplifier and phase delay circuitry, and a computer (e.g., a general-purpose computer) performing the computations and communicating the phases and amplitudes for the individual transducer elements 78 to the beamformer(s). Additionally, it is recognized that the controller 80 is operably connected to the computer 20 of MRI system 10, such that the controller 80 can control transducer 72 to time an application of focused ultrasound to a target tissue to coincide with generation/application of a pulse sequence from MRI system 10, to provide for MR-ARFI visualization of the applied ultrasound, as explained in greater detail below.

In performing of a focused ultrasound procedure for treating the target 76 in the ROI, the focus of the ultrasound can be visualized using MR-ARFI so as to confirm the location and measure the quality of the focus. In MR-ARFI, a transducer is driven so as to focus an ultrasound wave pulse into the body at or near the target. The ultrasound wave exerts acoustic radiation pressure onto the material along its path. At the focus, where the waves converge, this pressure is highest, resulting in a temporary local displacement of the material from equilibrium in the longitudinal direction and/or in shear waves that propagate radially away from the focus—with the displacement varying between about −1 μm and 5 μm depending on the intensity of the acoustic field. Thus, the ultrasound pressure creates a displacement field that directly reflects the acoustic field. The displacement field may be visualized by applying transient-motion or displacement-sensitizing magnetic field gradients to the imaging region by gradient coils, such as gradient coil assembly 50 in MR imaging system 10. When the ultrasound pulse is applied in the presence of such gradients, the resulting displacement is directly encoded into the phase of the MR response signal. For example, the gradient coils and transducer may be configured such that the ultrasound pulse pushes material near the focus towards regions of the magnetic field with higher field strengths. In response to the resulting change in the magnetic field, the phase of the MR response signal changes proportionally, thereby encoding in the signal the displacement caused by the ultrasound radiation pressure.

MR-ARFI may be used to "auto-focus" an ultrasound beam (i.e., to iteratively improve the focus quality of a pre-focused beam based on experimental feedback) in advance of the therapeutic application of ultrasound. Consider, for example, the treatment of a brain tumor with ultrasound. A transducer for such an application is usually large; it may surround a wide area of the skull and comprise a large number of elements (e.g., 1000). In preparation for treatment, the transducer is typically placed in a stable position relative to the patient's head, and the transducer elements are then activated at relative phases based on the sonication geometry (which generally includes the relative position and orientation of transducer and the target tissue, as well as the target location). Optionally, phase corrections may be applied to the transducer elements to compensate for tissue aberrations, which are mostly caused by the intervening skull tissue and which may vary significantly with location. The phase corrections may be computed based on skull-imaging data obtained through MR imaging, which provide estimates of the local skull bone thickness and density. Often, such computational correction for skull-based aberrations results in a noticeable, yet insufficient improvement of the focus quality. The focus may be optimized with an auto-focusing procedure, in which low-energy ultrasound is focused at (or near) the target, and a quantity correlated to the focus quality (e.g., the peak displacement caused by radiation force) is measured.

According to embodiments of the invention, auto-focusing is performed using MR-ARFI, with the ultrasound field being determined by measuring the relative tissue displacement that each transducer element produces. To address target tissue aberrations caused by bone and/or other intervening tissue(s), an autofocusing method is employed in embodiments of the present invention that uses the entire MR-ARFI image (i.e., analyzes voxels at the target/focus location (center of the focus) and voxels of a surrounding volume, such an entirety of a surrounding tissue) to determine the aberrations, with a corrective phase/amplitude for each transducer being calculated based on analysis of the MR-ARFI image. By using the entire MR-ARFI image to determine the aberrations rather than just the voxels at the center of the focus in the MR-ARFI image (as is done in some existing prior art techniques), the number of image acquisitions required to perform the autofocusing is dramatically reduced, thereby making MR-ARFI-based autofocusing clinically-feasible, and possible in near-real time.

Figure 2:
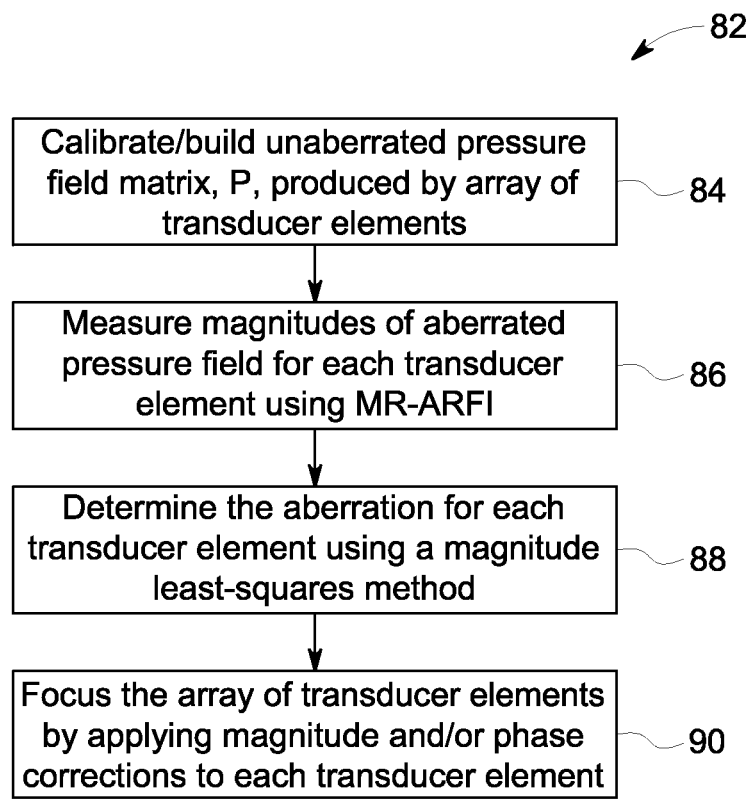
FIG. 2 is flowchart of a technique for autofocusing an ultrasound transducer array using MR-ARFI according to an embodiment of the invention.

Referring now to FIG. 2, a technique 82 for focusing a transducer array using MR-ARFI is illustrated according to an embodiment of the invention. As shown in FIG. 2, technique 82 begins by calibrating or building a pressure field matrix P at STEP 84 that is produced by transducer elements without aberration (i.e., unaberrated pressure field). The pressure field matrix P for the transducer elements is constructed/built offline (pre-calibrated or pre-computed) using MR-ARFI images of a phantom or tissue sample, for example. Alternatively, the pressure field matrix P could also be constructed using numerical simulations in various tissue types, and the appropriate simulation could be chosen in a manner tailored to the target tissue during focusing.

Technique 82 continues by measuring the magnitudes of aberrated pressure fields using MR-ARFI at STEP 86—with the pressure fields being aberrated based on the presence of bone or other intervening materials between the transducer and the target focus point. As set forth above, in MR-ARFI, the displacement field resulting from the acoustic radiation pressure generated by an ultrasound wave exerts may be visualized by applying transient-motion or displacement-sensitizing magnetic field gradients. When the ultrasound pulse is applied in the presence of such gradients, the resulting displacement is directly encoded into the phase of the MR response signal. For example, the gradient coils and transducer may be configured such that the ultrasound pulse pushes material near the focus towards regions of the magnetic field with higher field strengths. In response to the resulting change in the magnetic field, the phase of the MR response signal changes proportionally, thereby encoding in the signal the displacement caused by the ultrasound radiation pressure.

Upon measuring of the magnitudes of the aberrated pressure fields using MR-ARFI, the technique continues at STEP 88 where a determination of the aberrations is performed. In determining the aberrations, it is assumed that the HIFU pressure field in and around the focus can be expressed as the complex sum of the fields produced by the transducer elements, which are phase-shifted and attenuated by aberrations. In the absence of aberrations, the total HIFU pressure field is:

$$p(\vec{r}) = \sum_{n=1}^{N} p_n(\vec{r}) \tag{1},$$

where $p_n(\vec{r})$ is the complex-valued field produced by transducer element n, in the absence of aberrations. To a good approximation, aberrations and attenuations such as those produced by the skull can be expressed as a sum of phase-shifted and attenuated fields:

$$\tilde{p}(\vec{r}) = \sum_{n=1}^{N} a_n p_n(\vec{r}) \tag{2},$$

where the $a_n$ are complex-valued attenuation and phase aberrations.

If the transducer elements' pressure fields $p_n(\vec{r})$ and the total aberrated field $\tilde{p}(\vec{r})$ could be measured directly, then the aberrations could be determined by solving a system of linear equations. However, the MR-ARFI image is proportional to $|\tilde{p}(\vec{r})|^2$, with a constant of proportionality that is tissue-dependent—and thus the phase of $\tilde{p}(\vec{r})$ cannot be measured. As such, in STEP 88, a magnitude least-squares regression method is used to solve for the aberrations, given MR-ARFI images of $|\tilde{p}(\vec{r})|^2$ and a matrix of the individual elements' pressure fields $\tilde{p}(\vec{r})$. According to embodiments of the invention, various regressions could be implemented to solve for the aberrations, including a sum-of-squared errors, a maximum error norm, or a sum-of-absolute errors regression, for example. According to an exemplary embodiment, the magnitude least-squares method minimizes the following objective/cost function to solve for the length-n aberration vector a:

$$\Psi(a) = \sum_{l=1}^{L} ||\tilde{p}_l| - P\mathrm{diag}(w_n^l)a||_{W^l}^2 + R(a) \tag{3},$$

where the first term is formed by discretizing Eq. (2) and measuring the $l_2$ distance between right and left hand sides, summed across more than one image voxel. The variable l in Eq. (3) indexes the possibly multiple MR-ARFI acquisitions, each acquired with a possibly unique set of transducer element amplitudes and phase shifts $w^l$ that together produce L logical transducer elements. For example, the vectors $w^l$ could be Hadamard vectors of 1's and −1's. The pressure field matrix P (which has a row dimension equal to the number of voxels in the ARFI image, and column dimension equal to N) is known and provided from STEP 84, where P was constructed offline. Relative phases of the elements' ARFI images can be measured using an interference method, such as in: B. Larrat, M. Perrot, G. Montaldo, M. Fink, and M. Tanter, *MR-guided adaptive focusing of ultrasound*, IEEE Trans Ultrason Ferroelectr Freq Control, 57(8): 1734-1747, 2010.

It is noted that the array's physical elements could also be grouped into logical subsets, and that those subsets could be focused using this method. Further, in Eq. (3), the error weighting matrix $W_l$ can be used to account for variations in SNR and noise correlations between spatial locations, for example by setting $W_l = \text{diag}(|I_l(\vec{r}_j)|)$, where $I_l$ is one of the two complex-valued MR images from which $\tilde{p}_l$ was derived, and j indexes spatial locations. Finally, the regularization function R(a) could be constructed to, e.g., enforce smoothness of the aberrations between transducer elements, low integrated squared magnitude across the aberrations, or low total variation between adjacent aberrations.

Once the aberration vector a for each transducer element is computed at STEP 88 by minimizing the cost function in Eq. (3), the array is focused at STEP 90 by applying magnitude and/or phase corrections to each transducer element 78. To apply magnitude and phase corrections, each element's input signal is multiplied by a magnitude of its respective aberration vector $|a_n^{-1}|$, thereby imparting both a magnitude and phase correction. Alternatively, a phase-only correction can be achieved by adding angles of the respective aberration vectors $\angle a_n^{-1}$ to the phase of each transducer element's input signal.

Technique 82 thus provides an MR-ARFI-based autofocusing method that requires only a small number of image acquisitions, compared to the thousands required by existing methods, so as to enable autofocusing in a clinically-feasible time. The technique can be applied to focusing HIFU through any bones (including the skull), to focusing through inhomogeneous tissue (e.g., scars and fat between the transducer and the target focus), or to detecting the existence and position of ribs in front of the transducer, in order to switch off elements directly in front of the ribs.

Figure 3:
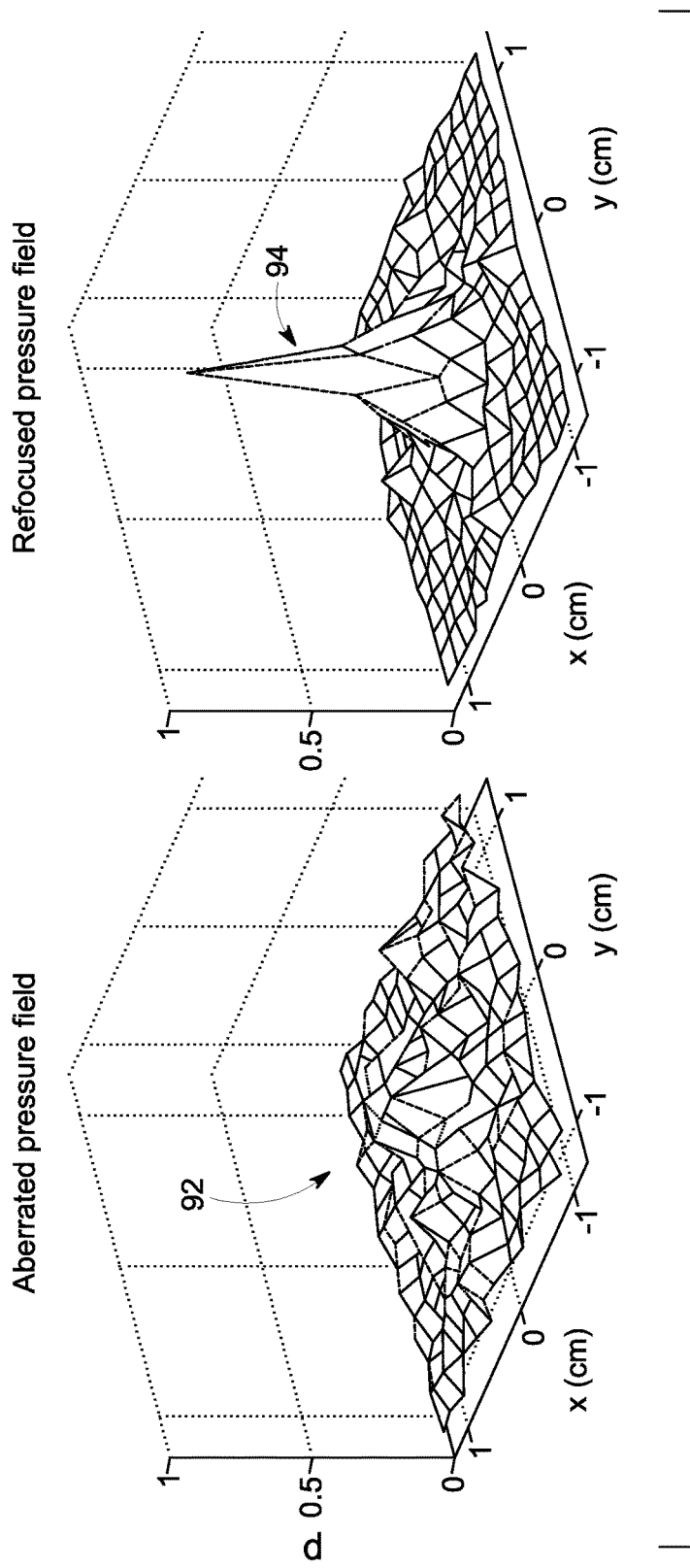
FIG. 3 is a graph illustrating an example of autofocusing achieved by implementing the technique of FIG. 2.

An example of autofocusing achieved by implementing technique 82 is illustrated in FIG. 3, where autofocusing was performed according to technique 82 after random phase aberrations were applied to the transducer. Using L=4 Hadamard encodings corresponding to 8 total MR image acquisitions, the technique restored the pressure field from an unfocused state, indicated at 92, to its focused state, indicated at 94. The eight (8) total MR image acquisitions is compared to a conventional method that required 6,144 total MR image acquisitions (i.e., 6 per transducer element, 6*1024).

It is recognized that, in implementing the MR-ARFI-based autofocusing method of the present invention, it is desirable that the MR pulse sequence used for image acquisition provide images that are free of distortions and signal loss induced by B0 and B1 inhomogeneity. That is, it is recognized that for certain HIFU applications, such as brain tumor treatment for example, where significant instrumentation is present inside the magnet bore of the MR system—e.g., helmet around the skull—significant B0 and B1 inhomogeneity is induced. In a brain application where the accuracy of ablation must be very high (<1 mm), such B0 and B1 inhomogeneity is highly undesirable as it can negatively affect the accuracy of the ablation. As such, it is desirable to provide a phase sensitive MR pulse sequence for image acquisition that will improve image quality in ARFI, with the use of such sequences in conjunction with the proposed MR-ARFI autofocusing technique 82 (and algorithm implemented therein) providing improved robustness and speed in the ultrasound autofocusing. While the MR pulse sequences described below are discussed with respect to use with ARFI, it is recognized that the pulse sequences are useful for a number of different MR imaging techniques that acquire phase sensitive data, such as temperature (PRF-shift) maps and Block-Siegert B1 maps, for example. Therefore, the pulse sequences described below are understood not to be limited for use only for ARFI applications.

With respect to designing a phase sensitive MR pulse sequence, the idea of using a Fast Spin Echo (FSE) echo train to measure phase was described in M. W. Vogel et. al., J. Mag. Res. Imag. Vol 18, p. 507-512 (2003), using a sophisticated phase modulation scheme. However, this method was not used in practice due to the need of a calibration which is sensitive to system imperfections. The separation of even and odd echoes to removed artifacts was introduced by Y. Zur and S. Stokar, J. Mag. Res. Vol 71, p. 212-228 (1987), using phase cycling and/or echo shifting. This echo time shift method was later used by D G Norris et. al. (Mag. Res. Med. Vol 27, p. 142, (1992)), F. Schick (Mag. Res. Med. Vol 38, p. 638 (1997)), and C Williams et. al. (Mag. Res. Med. Vol 41, p. 734 (1999)). Embodiments of the present invention separate even and odd echoes and add them coherently to enhance signal-to-noise ratio (SNR)—by 1.4—and eliminate echo oscillations while preserving the phase prior to the first refocusing RF pulse.

According to an exemplary embodiment, a phase sensitive FSE method is provided that measures the phase, $\phi_0$, induced by ARFI at each location, while being free of distortions and signal loss induced by B0 inhomogeneity. The phase $\phi_0$ (shown in FIG. 5 and Eq. (4)) is measured with the signals from an FSE echo train. The echo train consists of a large number, N, of echoes separated by a short echo time, such that a full image can be reconstructed using a single or a small number of echo trains. The phase of each voxel in the reconstructed image is proportional to $\phi_0$. This technique is based on the fact that the signal after each 180 pulse is broken into two echoes, with the phase difference between them being proportional to the phase prior to the first 180 pulse. Therefore, by separating the echoes, the phase prior to the FSE train—which can be caused by temperature change, ARFI, Bloch Siegert B1 shift, etc.—can be measured. By a proper combination of the two echoes, the signal becomes smooth and the signal-to-noise ratio (SNR) improves by, for example, a factor of 1.4. Additionally, since during data acquisition the signal is fully refocused, there are no spatial shifts or signal loss due to B0 inhomogeneity.

Figure 4:
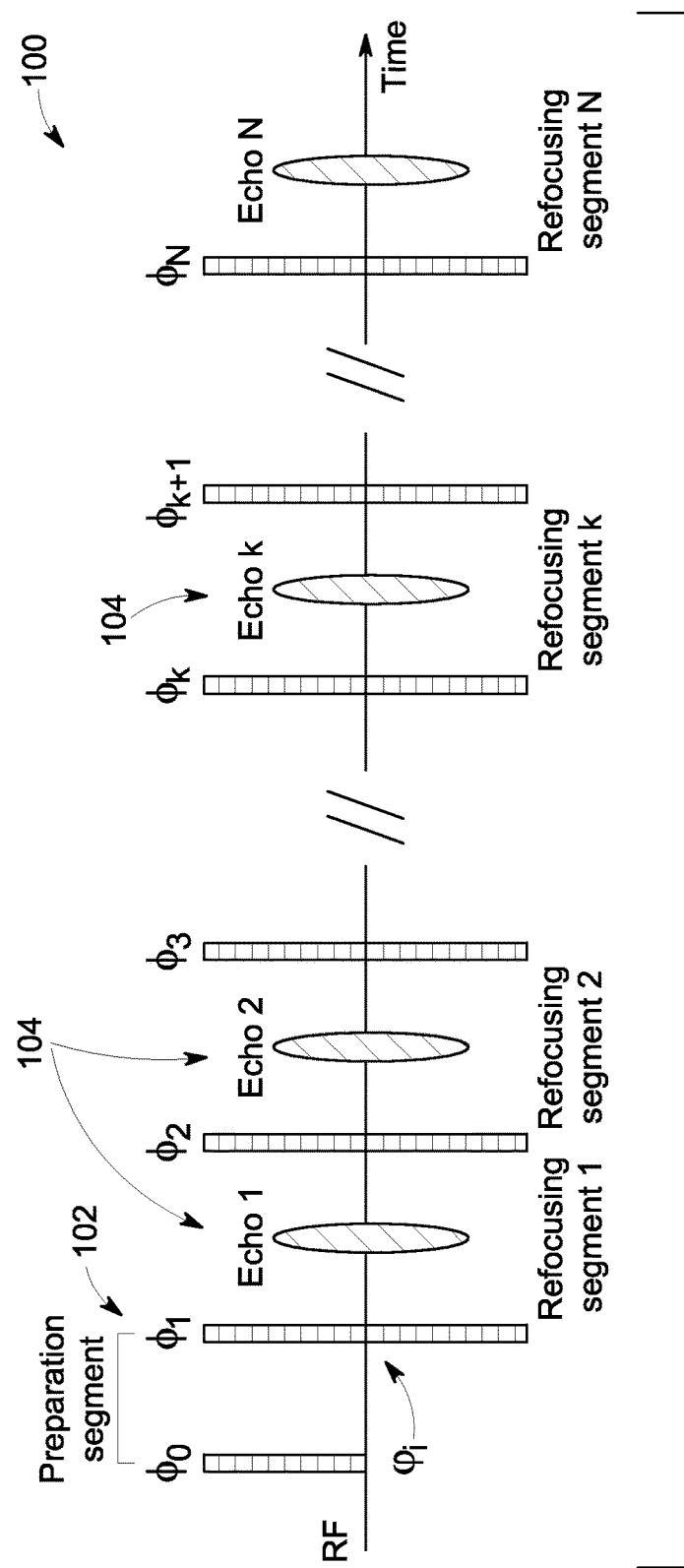
FIG. 4 is a diagram of a phase-sensitive fast spin echo (FSE) pulse sequence according to an embodiment of the invention.

In FIG. 4, a phase-sensitive FSE pulse sequence 100 is shown according to one embodiment. The FSE sequence 100 includes a preparation segment 102 and a sequence of N refocusing pulses applied during identical time segments, referred to below as refocusing segments 104. To distinguish between RF phases and magnetization (signal) phases, we use the letter φ for RF phases and ϕ for magnetization phases. The RF phase during refocusing segment k is $\varphi_k$, k=1 to N. The phase of the RF pulse in the preparation segment ("90°" RF pulse) is $\varphi_0$. $\phi_i$ is the phase accumulated during the preparation segment 102, and $\phi_0$ is the phase induced during the preparation segment 102 by thermal, ARFI, fMRI etc., that we want to measure. $\phi_i$ is given by:

$$\varphi_i = \phi_0 + \frac{\pi}{2} + \varphi_0. \tag{4}$$

Figure 5:
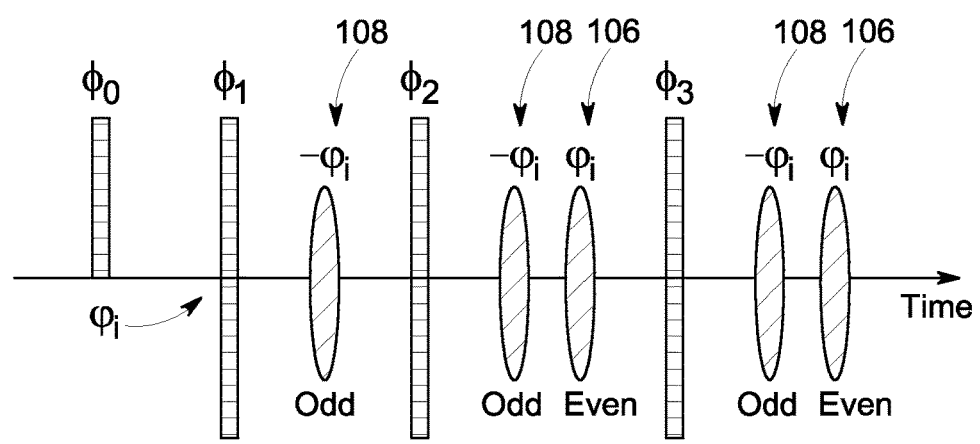
FIG. 5 is a diagram of a phase-sensitive fast spin echo (FSE) pulse sequence according to another embodiment of the invention.

Assuming that all refocusing segments 104 are identical and that the phases of all refocusing pulses are zero, the Meiboom-Gill condition is fulfilled if $\phi_i$ is zero. If $\phi_i \neq$, the signal in each segment 104 breaks into two echoes: 1) an "Even" echo 106 which is generated by magnetization pathways with an even number of phase inversions; 2) an "Odd" echo 108 which is generated by magnetization pathways with an odd number of phase inversions, as is shown in FIG. 5. The phase of the even echoes 106 is proportional to $\phi_i$ because the number of inversions is even. The phase of the odd echoes 108 is proportional to $-\phi_i$ because the number of inversions is odd. The goal is to find $\phi_i$ and $\phi_0$ (Eq. (4)) from the preparation segment 102. This is done by separating the even and the odd echoes 106, 108 and calculating the phase difference between them.

The even and odd echoes 106, 108 can be separated by 1) a two-shot phase cycling, or 2) by separating them in time in each refocusing segment (i.e., time shifting) and using a single shot, as explained below. In separating the echoes, the signal of the even echoes (with phase $\phi_i$) is added to the complex conjugate of the odd echoes signal (with phase $-\phi_i$) and a smooth signal is obtained with similar magnitude to the fully refocused FSE but with phase $\phi_i$.

In separating the even and odd echoes 106, 108 via a two-shot phase cycling, two shots with different RF phases are run. The general relation between the RF phases in these two shots required to separate the even and odd echoes is given by Y. Zur and S. Stokar, J. Mag. Res. Vol 71, p. 212-228 (1987). The simplest combination according to:

$$\text{shot 1} \quad \phi_0 = 0 \quad \phi_k = 0 \quad \text{for all } k = 1 \text{ to } N \tag{5a}$$

$$\text{shot 2} \quad \phi_0 = -\frac{\pi}{2} \quad \phi_k = 0 \quad \text{for all } k = 1 \text{ to } N. \tag{5b}$$

The phase of the echoes in each shot is the same during all N refocusing segments.

In shot 1:

phase of even echoes=$\pi/2+\phi_0$ and phase of odd echoes=$-\pi/2-\phi_0$ (6a).

In shot 2:

phase of even echoes=$\phi_0$ and phase of odd echoes=$-\phi_0$ (6b).

Figure 6A:
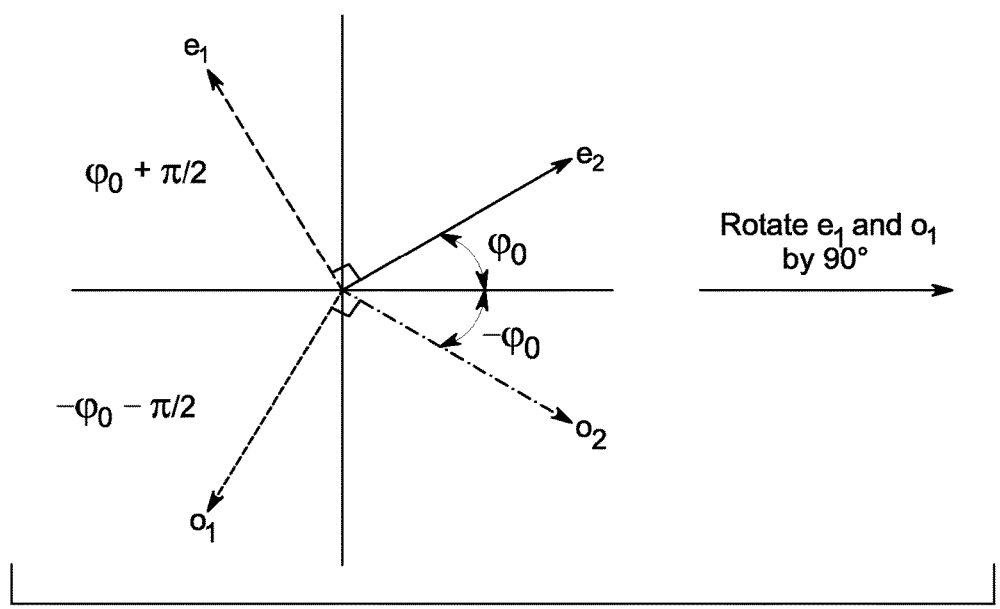
FIGS. 6A-6D are diagrams of a separation and combination of even and odd echoes according to an embodiment of the invention.
Figure 6B:
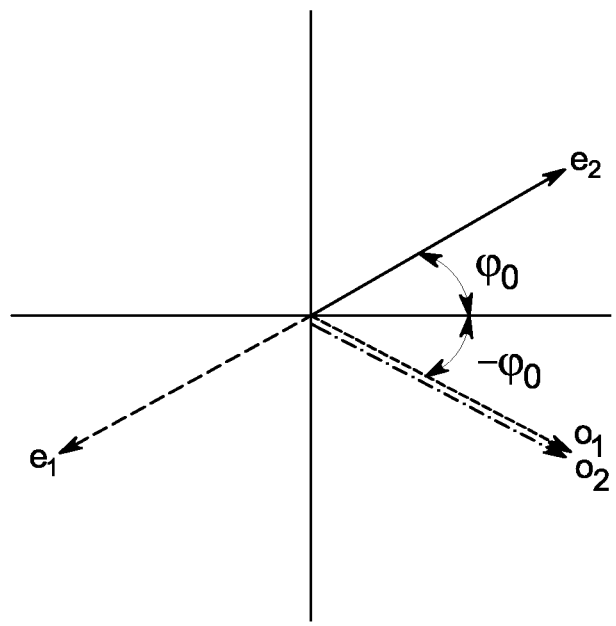
Figure 6C:
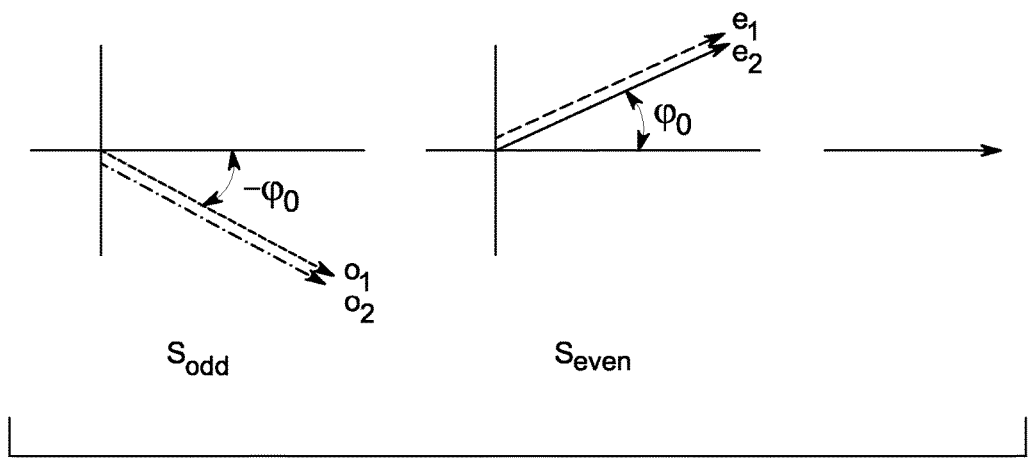
Figure 6D:
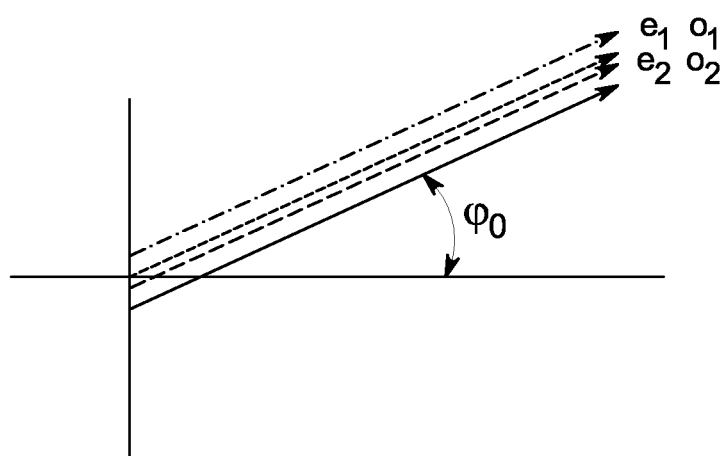

The separation of the even echo $S_{even}$ and the odd echo $S_{odd}$ using the signals $S_1$ and $S_2$ of shots 1 and 2 is shown in FIGS. 6A-6D, with FIG. 6A showing even and odd echoes from the signals $S_1$ and $S_2$ of shots 1 and 2, FIG. 6B showing $S_1$ rotated by 90°—such that the even echoes e1, e2 are opposite to each other and odd echoes o1, o2 are in phase, FIG. 6C showing the even and odd echoes being separated by subtraction and addition of $iS_1$ and $S_2$, and FIG. 6D showing the even echo $S_{even}$ and the complex conjugate of the odd echo $S_{odd}$ being aligned, generating the signal S with phase $\phi_0$. From FIGS. 6A-6D:

$$S_{odd} = \frac{iS_1 + S_2}{2}; S_{even} = \frac{iS_1 - S_2}{2}. \tag{7a}$$

The final image S with phase $\phi_0$ is obtained by $$S = S_{even} + S^*_{odd} \tag{7b}.$$

In practice the phases of the even (odd) echoes may have error term $\phi_{E1}$ ($\phi_{E2}$) respectively due to misplaced sampling window, eddy currents etc.

In shot 1:

phase of even echoes=$\pi/2+\phi_0+\phi_{E1}$ and phase of odd echoes=$-\pi/2-\phi_0+\phi_{E2}$ (8a).

In shot 2:

phase of even echoes=$\phi_0+\phi_{E1}$ and phase of odd echoes=$-\phi_0+\phi_{E2}$ (8b).

The even and odd echoes are separated using Eq. (7a), but the phases are $\phi_0+\phi_{E1}$ and $-\phi_0+\phi_{E2}$. For any phase sensitive scan (thermal, ARFI, $b_1$, etc.), a reference scan is acquired prior to heating, where $\phi_0=0$, to remove irrelevant error phase such as $\phi_{E1}$ and $\phi_{E2}$. After removing the error phase, the phase of the even and odd echoes is given by (6a) and (6b) and the echoes are combined as in (7b).

Figure 7:
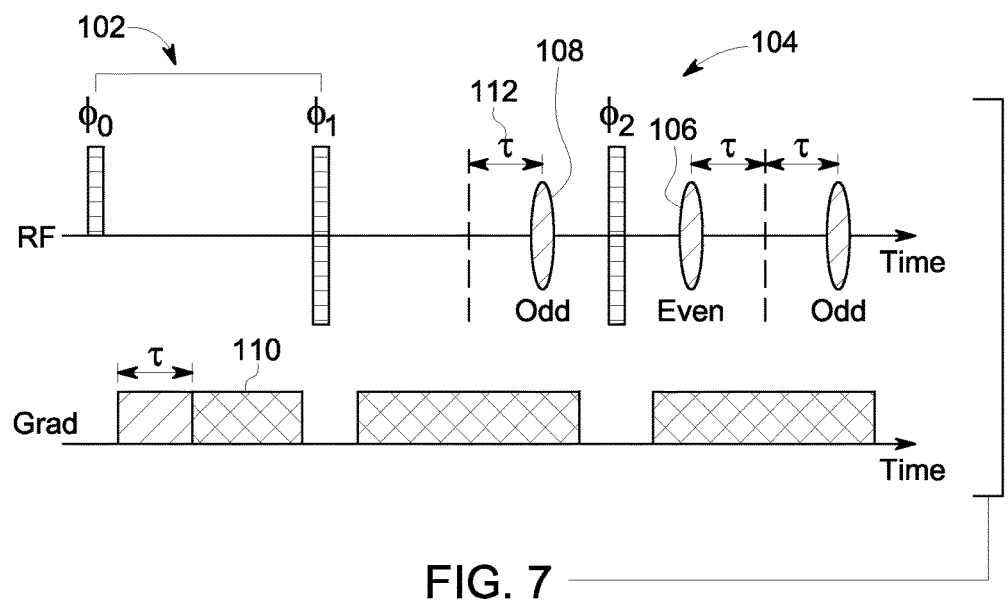
FIG. 7 is a diagram of a phase-sensitive fast spin echo (FSE) pulse sequence according to another embodiment of the invention.

It is possible to separate even and odd echoes 106, 108 via time shifting, by adding a read gradient 110 of duration $\tau$ sec in the preparation segment 102, the even (odd) echo in each refocusing segment 104 shifts to the left (right) by $\tau$ sec, indicated at 112, as shown in FIG. 7. Each echo 106, 108 is sampled in a separate sampling window, and the phase difference is used to measure $\phi_0$. The even and the odd echoes 106, 108 are combined to a signal S as in Eq. (7b), where S varies smoothly in time and has the same amplitude as the conventional single shot FSE signal.

While only a single shot is required to separate the echoes 106, 108, the drawback of the method is the need to use two sampling windows in each refocusing segment 104 (FIG. 5), so the time distance between two adjacent refocusing pulses (esp) is doubled, resulting in contrast and signal to noise reduction In addition, the signal of each echo group (even and odd) is very oscillatory. A coherent addition is very sensitive to system imperfection and not practical in practice, as described in C Williams et al. Mag. Res. Med. Vol. 41, p. 734 (1999).

According to one embodiment of the invention, the number of k space lines in each echo train may be reduced using parallel imaging. In the first shot, the odd k-space lines (1, 3, 5, . . . ) are acquired, and in the second shot, even lines (2, 4, 6, . . . ) are acquired. In this case, the unacquired lines are calculated using parallel imaging with acceleration R=2 to separate even and odd echoes.

Figure 8:
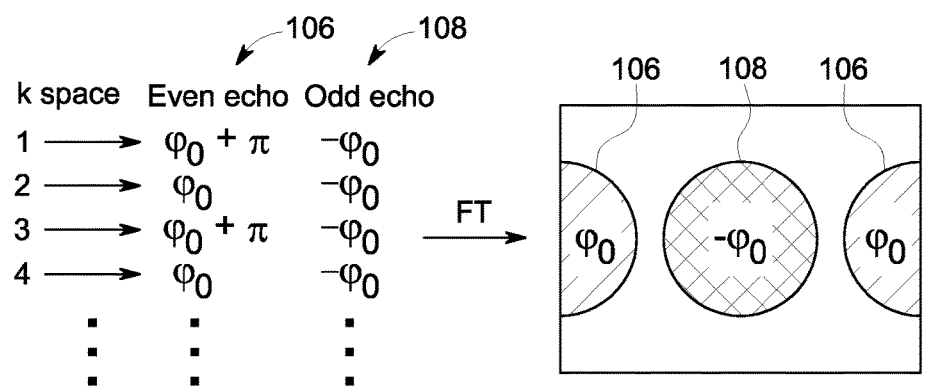
FIG. 8 is a table and diagram illustrating the phase of even and odd echoes for each of odd k-space lines and even k-space lines and a shifting of the image of the even echoes by half a FOV with respect to the image of the odd echoes, according to an embodiment of the invention.

As shown in FIG. 8, if the RF phases of Eq. (5) are used, the phase of the even echo of $iS_1$ (i=sqrt(−1)) and S2 (Eq. [3]) are $\phi_0+\pi$ and $\phi_0$ respectively and the phase of the odd echo of $iS_1$ and $S_2$ are $-\phi_0$ and $-\phi_0$ respectively. During the first FSE shot (where odd k-space lines are acquired) we use the RF phases of Eq. (5a) and during the second shot (even k-space lines) the phases of Eq. (5b). Therefore the phase of the even echo 106 for even and odd k-space lines is $\phi_0+\pi$, and $\phi_0$ respectively. The phase of the odd echo 108 for even and odd k-space lines is $-\phi_0$, and $-\phi_0$ respectively. Hence, after Fourier transform, the image of the even echoes 106 (with phase $\phi_0$) is shifted by half FOV with respect to the image of the odd echoes 108 (with phase $-\phi_0$) along the phase encode direction, as shown in FIG. 8. Due to this shift the geometry factor (g factor) of the images decreases significantly, as described in F. A. Breuer et. al., Mag. Res. Med, Vol. 53, p. 684-691 (2005), so the images of the even and odd echoes can be faithfully reconstructed with R=2 parallel imaging.

In implementing embodiments of the invention, it is recognized that in most cases the area of interest for thermal and ARFI applications is limited, e.g. 5 to 10 cm. Therefore, for a given spatial resolution, a much lower number of phase encoding lines are required, provided that the signal from spins outside the limited FOV of 5 to 10 cm can be suppressed. This is very useful for the ssFSE scan, because a much lower number of echoes need to be acquired in a single shot.

According to one embodiment of the invention, a technique for suppressing a signal from outside the restricted FOV is provided in which different slice-select gradients are applied during the preparation segment RF pulse ("90°") and during the refocusing RF pulses. Application of the slice-select gradients at these times ensures that only spins at the cross-section of the slices excited by both RF pulses are detected. The drawback of this technique is that the multi-slice capability of ssFSE is lost, since the RF pulses excite along two orthogonal directions.

Figure 9:
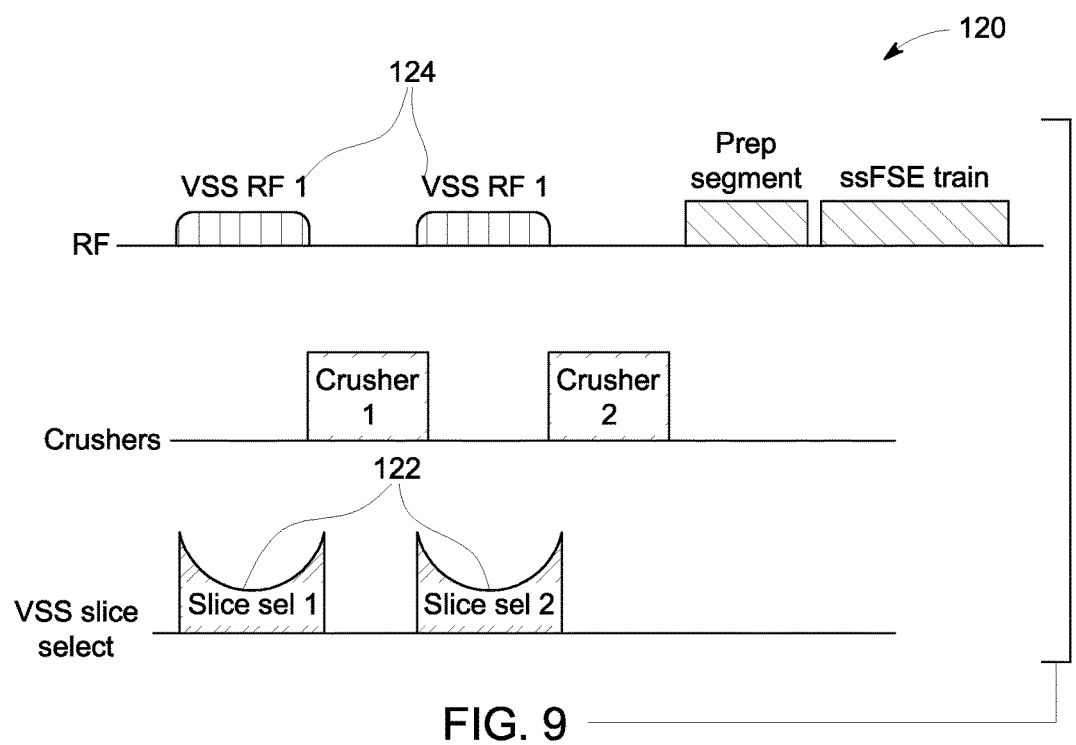
FIG. 9 is a diagram of a restricted FOV phase-sensitive fast spin echo (FSE) pulse sequence according to another embodiment of the invention.

Referring to FIG. 9, a pulse sequence 120 for suppressing a signal from outside the restricted FOV is provided according to one embodiment of the invention. In the sequence, slice select variable rate selective excitation (VERSE) gradients 122 are applied in the phase direction, so the FOV along the phase is restricted to about 10 cm—with the slice select VERSE gradients being applied prior to the ssFSE preparation segment and ssFSE train. Additionally, the sequence 120 applies a train of up to three multi-band quadratic phase RF pulses 124 that saturate the spins above and below the restricted FOV. It can be shown that in case of $b_1$ inhomogeneity, a train of three RF pulses achieves perfect suppression even with $b_1$ variation of 100%. However, in most cases a single RF pulse is sufficient. The quadratic phase RF pulses 124 are low power with very high time-bandwidth product. In this way, robust signal suppression is obtained without losing the multi-slice capability.

Therefore, according to embodiments of the invention shown and described in FIGS. 4-9, complimentary FSE and ssFSE sequences are provided that will improve image quality in ARFI and other phase-based MR imaging techniques. Use of these sequences in conjunction with the proposed MR-ARFI autofocusing algorithm in technique 82 will dramatically improve the robustness and speed of ultrasound autofocusing.

Beneficially, embodiments of the invention thus provide an MR-ARFI-based autofocusing method that requires only a small number of image acquisitions, compared to the thousands required by current methods, so as to enable autofocusing in a clinically-feasible time. The method could be applied to focusing HIFU through any bones including the skull, to focusing through inhomogeneous tissue (e.g., scars and fat between the transducer and the target focus), or to detecting the existence and position of ribs in front of the transducer, in order to switch off elements directly in front of the ribs. The technique enables real-time acquisition of ARFI images that are free of spatial distortion and signal loss.

A technical contribution of the invention is that it provides a computer implemented technique for MR-ARFI-based autofocusing of focused ultrasound that requires only a small number of image acquisitions.

One skilled in the art will appreciate that embodiments of the invention may be interfaced to and controlled by a computer readable storage medium having stored thereon a computer program. The computer readable storage medium includes a plurality of components such as one or more of electronic components, hardware components, and/or computer software components. These components may include one or more computer readable storage media that generally stores instructions such as software, firmware and/or assembly language for performing one or more portions of one or more implementations or embodiments of a sequence. These computer readable storage media are generally non-transitory and/or tangible. Examples of such a computer readable storage medium include a recordable data storage medium of a computer and/or storage device. The computer readable storage media may employ, for example, one or more of a magnetic, electrical, optical, biological, and/or atomic data storage medium. Further, such media may take the form of, for example, floppy disks, magnetic tapes, CD-ROMs, DVD-ROMs, hard disk drives, and/or electronic memory. Other forms of non-transitory and/or tangible computer readable storage media not list may be employed with embodiments of the invention.

A number of such components can be combined or divided in an implementation of a system. Further, such components may include a set and/or series of computer instructions written in or implemented with any of a number of programming languages, as will be appreciated by those skilled in the art. In addition, other forms of computer readable media such as a carrier wave may be employed to embody a computer data signal representing a sequence of instructions that when executed by one or more computers causes the one or more computers to perform one or more portions of one or more implementations or embodiments of a sequence.

Therefore, according to one embodiment of the invention, a magnetic resonance (MR) imaging system includes a plurality of gradient coils positioned about a bore of a magnet, an RF coil assembly configured to emit RF pulse sequences and arranged to receive resulting MR signals from a subject of interest, and a system control coupled to the plurality of gradient coils and the RF coil assembly, the system control programmed to control the RF coil assembly and the plurality of gradient coils to apply a fast spin echo (FSE) pulse sequence comprising a preparation segment and a plurality of refocusing segments, wherein a pair of echoes is generated in each of the plurality of refocusing segments that comprises a first echo generated by magnetization pathways having an even number of phase inversions and a second echo generated by magnetization pathways having an even number of phase inversions. The MR imaging system also includes a computer programmed to acquire the MR signals from the first echo and the second echo and reconstruct an image of at least a portion of the subject of interest from the acquired MR signals.

According to another embodiment of the invention, a method for magnetic resonance (MR) imaging includes causing an MR imaging system to apply a fast spin echo (FSE) pulse sequence comprising a preparation segment and a plurality of refocusing segments, wherein applying the FSE pulse sequence further includes applying a 90° RF pulse in the preparation segment and applying a 180° RF pulse in each of the plurality of refocusing segments. The method also includes causing the MR imaging system to acquire MR image data from a pair of echoes in each of the plurality of refocusing segments, the pair of echoes comprising a first echo generated by magnetization pathways having an even number of phase inversions and a second echo generated by magnetization pathways having an even number of phase inversions, and causing a processor in the MR imaging system to generate an image from the acquired MR image data.

According to yet another embodiment of the invention, a non-transitory computer readable storage medium is provided having stored thereon a computer program comprising instructions that, when executed by a computer, cause the computer to request transmission of a 90° RF pulse during a preparation segment of a fast spin echo (FSE) pulse sequence and request transmission of a 180° RF pulse during each of a plurality of refocusing segments of the FSE pulse sequence, with each 180° RF pulse generating a first echo and a second echo in its respective refocusing segment. The instructions further cause the computer to separate the first echo from the second echo, acquire magnetic resonance (MR) signals from the first and second echoes, calculate a phase difference between the MR signals from the separated first and second echoes, combine the MR signals from the separated first and second echoes based on the phase difference there between in order to reduce a signal-to-noise ratio (SNR) of the MR signals, and generate an MR image based on the MR signals.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A magnetic resonance (MR) imaging system comprising:
   a plurality of gradient coils positioned about a bore of a magnet;
   an RF coil assembly configured to emit RF pulse sequences and arranged to receive resulting MR signals from a subject of interest;
   a system control coupled to the plurality of gradient coils and the RF coil assembly, the system control programmed to control the RF coil assembly and the plurality of gradient coils to apply a fast spin echo (FSE) pulse sequence comprising a preparation segment and a plurality of refocusing segments, wherein a pair of echoes is generated in each of the plurality of refocusing segments that comprises:
      a first echo generated by magnetization pathways having an even number of phase inversions; and
      a second echo generated by magnetization pathways having an odd number of phase inversions; and
   a computer programmed to:
      acquire the MR signals from the first echo and the second echo; and
      reconstruct an image of at least a portion of the subject of interest from the acquired MR signals.

2. The MR imaging system of claim 1, wherein the computer is further programmed to:
   separate the first echo from the second echo; and
   calculate a phase difference between the separated first and second echoes.

3. The MR imaging system of claim 2, wherein, in separating the first echo from the second echo, the system control is programmed to control the RF coil assembly and the plurality of gradient coils to apply a two-shot single-shot fast spin echo (two-shot ssFSE) sequence to separate the first and second echoes, with RF pulses in a preparation segment of a first shot and a preparation segment of a second shot having different phases.

4. The MR imaging system of claim 3, wherein the computer is further programmed to:
   acquire odd k-space data lines in the first shot using an RF pulse in the preparation segment of the first shot having a first phase;
   acquire even k-space data lines in the second shot using an RF pulse in the preparation segment of the second shot having a second phase different from the first phase; and
   calculate unacquired k-space data lines from the first and second shots using a parallel imaging technique with the two-shot ssFSE sequence, such that images of the first and second echoes can be fully reconstructed with the two-shot ssFSE sequence.

5. The MR imaging system of claim 2, wherein in separating the first echo and the second echo, the system control is programmed to apply a readout gradient pulse to the preparation segment so as to shift the first echo in each refocusing segment, such that the first and second echoes are sampled in different sampling windows.

6. The MR imaging system of claim 2, wherein the computer is further programmed to determine a phase accumulated during the preparation segment and a phase induced during the preparation segment by a magnetic resonance acoustic radiation force impulse (MR-ARFI) image acquisition based on the calculated phase difference between the first echo and the second echo.

7. The MR imaging system of claim 1, wherein the system control is programmed to control the plurality of gradient coils to apply different slice-select gradients during the preparation segment and during the plurality of refocusing segments.

8. The MR imaging system of claim h wherein an RF pulse in the FSE pulse sequence applied in the preparation segment comprises a 90° pulse and an RF pulse in the FSE pulse sequence applied in each of the plurality of refocusing segments comprises a 180° pulse.

9. The MR imaging system of claim 1, wherein the MR signal of the first echo is added to a complex conjugate of the MR signal of the second echo, with a magnitude of the added MR signal of the first echo and the complex conjugate of the MR signal of the second echo being equal to a fully refocused fast spin echo.

10. A method for magnetic resonance (MR) imaging comprising:
   causing an MR imaging system to apply a fast spin echo (FSE) pulse sequence comprising a preparation segment and a plurality of refocusing segments, wherein applying the FSE pulse sequence includes:
      applying a 90° RF pulse in the preparation segment;
      applying a 180° RF pulse in each of the plurality of refocusing segments;
   causing the MR imaging system to acquire MR image data from a pair of echoes in each of the plurality of refocusing segments, the pair of echoes comprising:
      a first echo generated by magnetization pathways having an even number of phase inversions; and
      a second echo generated by magnetization pathways having an odd number of phase inversions; and causing a processor in the MR imaging system to generate an image from the acquired MR image data.

11. The method of claim 10, further comprising causing the processor in the MR imaging system to:
separate the first echo from the second echo; and
calculate a phase difference between the separated first and second echoes.

12. The method of claim 11, wherein in separating the first echo from the second echo, the MR imaging system is further caused to run a first shot and a second shot, with RF pulses in a preparation segment of the first shot and a preparation segment of the second shot having different phases.

13. The method of claim 12, further comprising causing the processor in the MR imaging system to:
acquire odd k-space data lines in the first shot;
acquire even k-space data lines in the second shot; and
calculate unacquired k-space data lines from the first and second shots using parallel imaging.

14. The method of claim 13, wherein in separating the first echo from the second echo, the MR imaging system is further caused to apply a readout gradient pulse to the preparation segments so as to shift the first echo in each refocusing segment, such that the first and second echoes are sampled in different sampling windows.

15. The method of claim 11, further comprising causing the processor in the MR imaging system to determine a phase accumulated during the preparation segment and a phase induced during the preparation segment by a magnetic resonance acoustic radiation force impulse (MR-ARFI) image acquisition based on the calculated phase difference between the first echo and the second echo.

16. The method of claim 10, further comprising causing a plurality of gradient coils in the MR imaging system to apply different slice-select gradients during the preparation segment and during the plurality of refocusing segments.

17. A non-transitory computer readable storage medium having a computer program stored thereon and representing a sequence of instructions that when executed by a computer causes the computer to:
request transmission of a 90° RF pulse during a preparation segment of a fast spin echo (FSE) pulse sequence;
request transmission of a 180° RF pulse during each of a plurality of refocusing segments of the FSE pulse sequence, with each 180° RF pulse generating a first echo and a second echo in its respective refocusing segment;
separate the first echo from the second echo;
acquire magnetic resonance (MR) signals from the first and second echoes;
calculate a phase difference between the MR signals from the separated first and second echoes;
combine the MR signals from the separated first and second echoes based on the phase difference there between in order to reduce a signal-to-noise ratio (SNR) of the MR signals; and
generate an MR image based on the MR signals.

18. The non-transitory computer readable storage medium of claim 17, wherein the first echo is generated by magnetization pathways having an even number of phase inversions and the second echo is generated by magnetization pathways having an odd number of phase inversions.

19. The non-transitory computer readable storage medium of claim 17, wherein in requesting transmission of the 90° RF pulse and the 180° RF pulse, the instructions further cause the computer to:
request transmission of a two-shot single-shot fast spin echo (two-shot ssFSE) sequence to separate the first and second echoes for each shot, wherein a first shot of the two-shot ssFSE sequence acquires odd k-space lines using an RF pulse in a preparation segment having a first phase and wherein a second shot of the two-shot ssFSE sequence acquires even k-space lines using an RF pulse in a preparation segment having a second phase different from the first phase; and
employ a parallel imaging technique with the two-shot ssFSE sequence, such that images of the first and second echoes can be fully reconstructed with the two-shot ssFSE sequence.

20. The non-transitory computer readable storage medium of claim 17, wherein in separating the first echo from the second echo, the instructions further cause the computer to request transmission of a readout gradient pulse to the preparation segment so as to shift the first echo in each refocusing segment, such that the first and second echoes are sampled in different sampling windows.

* * * * *